US00PP37272P2

(12) United States Plant Patent
Moon

(10) Patent No.: US PP37,272 P2
(45) Date of Patent: Feb. 17, 2026

(54) ***QUERCUS VIRGINIANA* TREE NAMED 'QVMTF2'**

(50) Latin Name: *Quercus virginiana*
Varietal Denomination: QVMTF2

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 19/083,836

(22) Filed: Mar. 19, 2025

(51) Int. Cl.
*A01H 5/00* (2018.01)
*A01H 6/00* (2018.01)

(52) U.S. Cl.
USPC ..... Plt./225

(58) Field of Classification Search
USPC ..... Plt./225
See application file for complete search history.

*Primary Examiner* — Susan Mccormick Ewoldt
*Assistant Examiner* — Zachariah Allan Kay

(57) ABSTRACT

A new and distinct cultivar of *Quercus virginiana* tree named 'QVMTF2' is disclosed, characterized by a distinctively tight upright and full canopy. Foliage is glossy and dark green. Cold hardiness has been observed. The new variety is a *Quercus* tree, typically used for landscapes and gardens.

2 Drawing Sheets

Figure 1:
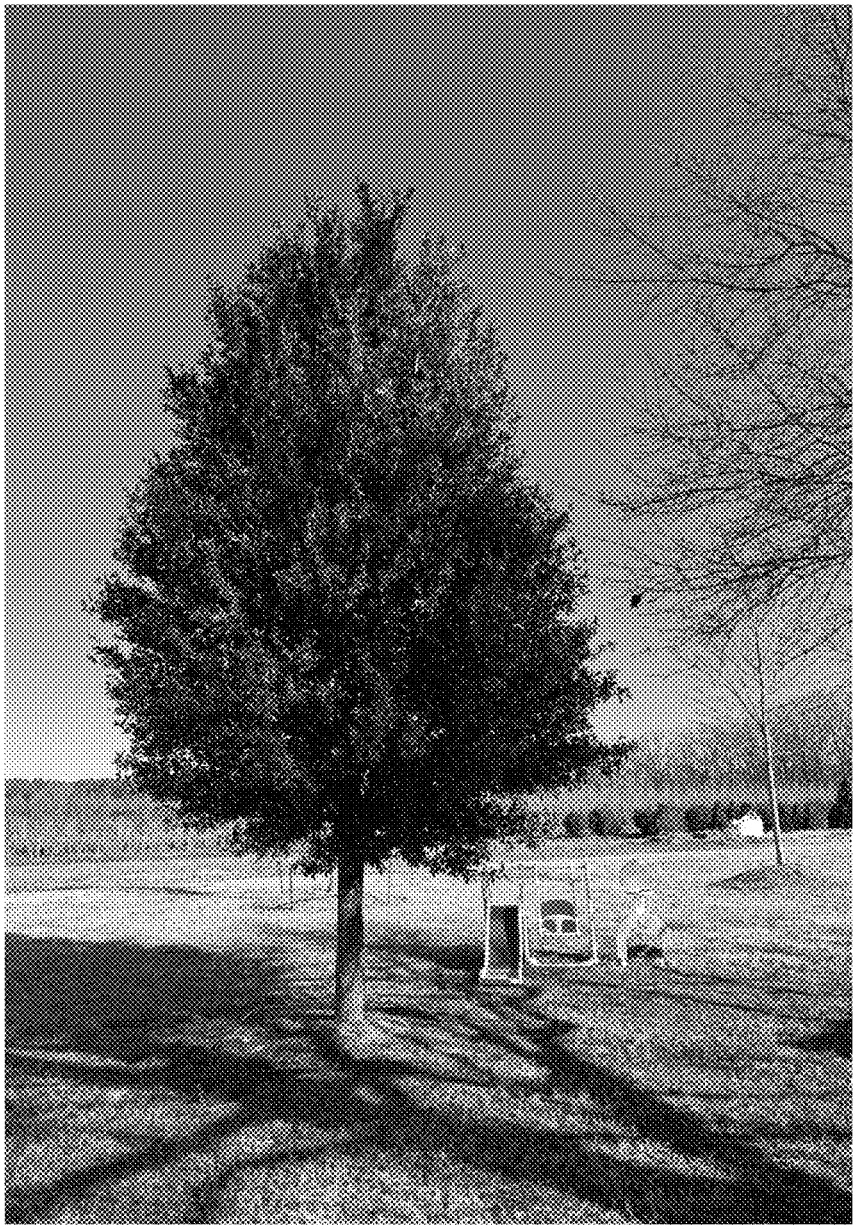

Latin name of the genus and species: *Quercus virginiana.*
Variety denomination: 'QVMTF2'.

BACKGROUND OF THE INVENTION

The new cultivar is a product of a planned breeding program. The new variety was discovered growing as a seedling among a group of open-pollinated Quercus virginiana trees at a tree farm in Washington, Georgia. A single seedling tree was observed which had distinctly dark green and glossy foliage. The inventor made this discovery in 2017. The exact seed and pollen parents cannot be identified.

Asexual reproduction by grafting of the new cultivar 'QVMTF2' was first performed in 2018 at a farm in Washington, Georgia. The cleft grafting system developed by the inventor has resulted in progeny that have proven the characteristics of the new variety to be genetically stable. This grafting process involved taking cuttings in February, being grafted, and being placed in calloused chambers for approximately three weeks. They are then moved into 3"x6" tree band pots and placed in humidity chambers for approximately four weeks. Furthermore, these observations have confirmed that the new variety represents a new and improved variety of *Quercus virginiana* tree as particularly evidenced by the tight, upright, full canopy and large dark green leaf. These genetic traits can be consistently reproduced by asexual propagation.

SUMMARY OF THE INVENTION

The cultivar 'QVMTF2' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'QVMTF2' grown in Washington, Georgia. These characteristics in combination distinguish 'QVMTF2' as a new and distinct *Quercus virginiana* cultivar:

1. Cold hardy.
2. Tight upright shape.
3. Full canopy.
4. Dark green large leaf.

PARENT COMPARISON

The exact parent varieties cannot be identified.

COMMERCIAL COMPARISON

Plants of the new cultivar 'QVMTF2' are similar to plants of *Quercus virginiana* 'SDLN', U.S. Plant Pat. No. 12,015, in most horticultural characteristics, however, plants of the new cultivar 'QVMTF2' differ in the following:

1. Foliage of the new variety is approximately double the size of foliage of this comparator.
2. Canopy of the new variety is more oval in shape with age; the canopy of this comparator remains pyramidal.

Plants of the new cultivar 'QVMTF2' are similar to plants of *Quercus virginiana* 'FBQV22', U.S. Plant Pat. No. 19,758, in most horticultural characteristics, however, plants of the new cultivar 'QVMTF2' differ in the following:

1. Canopy of the new variety is more oval in shape with age; the canopy of this comparator remains pyramidal.
2. Foliage of the new variety is approximately 70% larger than foliage of this comparator.

Plants of the new cultivar 'QVMTF2' are similar to plants of *Quercus virginiana* 'Cannon-Sharp', U.S. Plant Pat. No. 19,608, in most horticultural characteristics, however, plants of the new cultivar 'QVMTF2' differ in the following:

1. Foliage of the new variety is more than double the size of foliage of this comparator.
2. The new variety produces branches at more acute angles than branches of this comparator.

Plants of the new cultivar 'QVMTF2' are similar to plants of *Quercus virginiana* 'QVMTFS', U.S. Plant Pat. No. 35,315, in most horticultural characteristics, however, plants of the new cultivar 'QVMTF2' differ in the following:

1. Foliage of the new variety is about 20 to 40% larger than of foliage of this comparator.

2. The new variety has a denser canopy than this comparator.
3. The new variety does not produce the elongated new growth shoots found on this comparator.

Plants of the new cultivar 'QVMTF2' are similar to plants of *Quercus virginiana* 'QVTIA', U.S. Plant Pat. No. 11,219, in most horticultural characteristics, however, plants of the new cultivar 'QVMTF2' differ in the following:

1. The new variety has a more oval shape; this comparator has a pyramidal habit.
2. Foliage of the new variety does not have the lower surface pubescence found on foliage of this comparator.

Plants of the new cultivar 'QVMTF2' are similar to plants of *Quercus virginiana* 'CLTF2', U.S. Plant Pat. No. 11,097, in most horticultural characteristics, however, plants of the new cultivar 'QVMTF2' differ in the following:

1. Foliage of the new variety is dark green; foliage of this comparator is yellow-green.
2. Foliage of the new variety is about 20 to 40% smaller than foliage of this comparator.
3. Trees of the new variety do not grow as fast as trees of this comparator.

BRIEF DESCRIPTION OF THE PHOTOGRAPHS

The accompanying photograph in FIG. 1 illustrates a typical tree of the new variety at about 7 years of age during winter.

Figure 2:
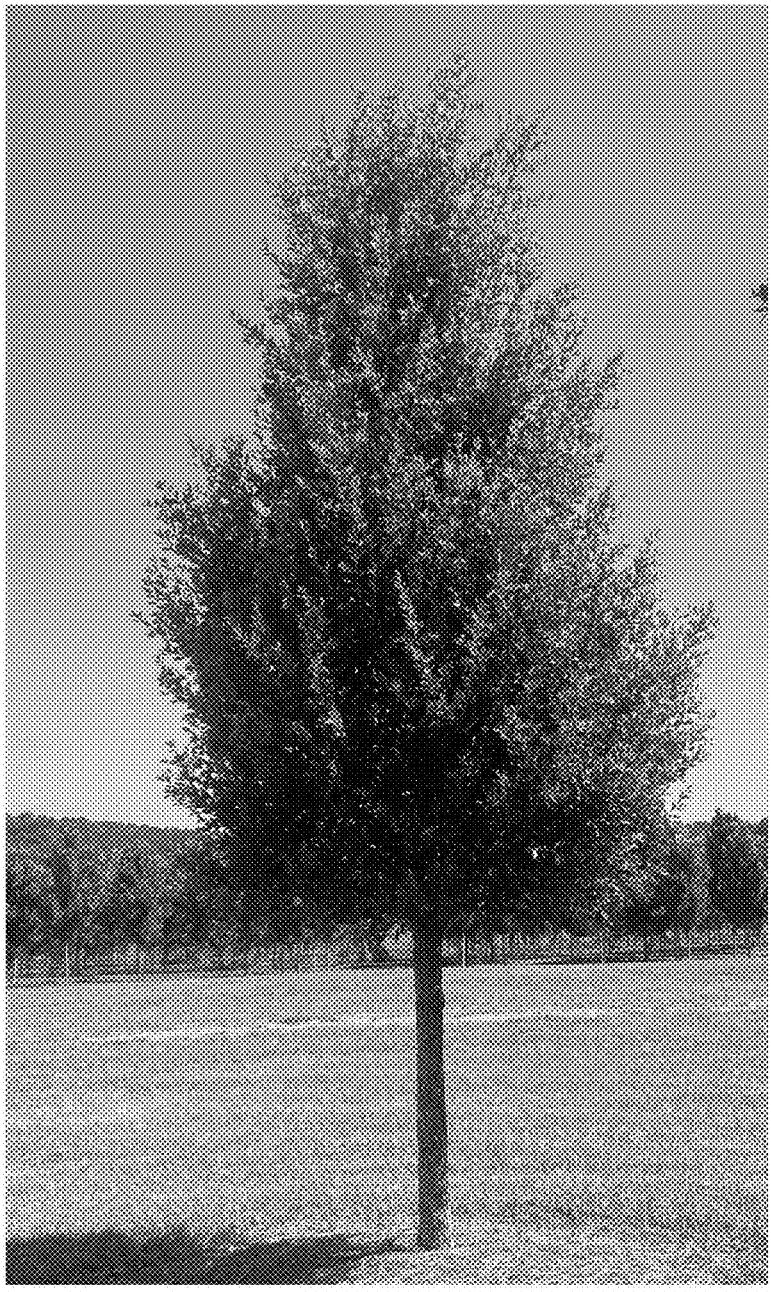

FIG. 2 illustrates a typical tree of the new variety at about 5 years of age during summer. The photographs were taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society Colour Chart 2015 except where general terms of ordinary dictionary significance are used. The following observations and measurements describe 'QVMTF2' plants grown outdoors and in a nursery in Washington, Georgia. Plants are approximately 2 years old, in a 3 gallon nursery container unless otherwise noted. Temperatures ranged from 5° C. to 10° C. at night to 18° C. to 27° C. during the day. Measurements and numerical values represent averages of typical plant types.

Botanical classification: *Quercus virginiana* 'QVMTF2'.

PROPAGATION

Cleft grafting.

Root Description: Dense and fibrous. Colored near Grey-Brown 199D and Yellow-White 158C.

TREE

Growth Habit: Evergreen tree with a dense, oval-shaped canopy.

Growth Rate: Approximately 1 inch of caliper per year.

Branch Aspect and Angle: Lower branches at angles of about 45 to 60 degrees from center. Upper branches 45 degrees or less from center.

Branch/Stem color:

*New Growth*.—Near RHS Greyed-Green 195A.

*Mature*.—Near RHS Greyed-Green 198B, speckles or streaks near Greyed-Orange 166C.

Trunk Characteristics:

*Diameter*.—About 7 mm on sapling. About 4.5 inches measured at approximately 3 inches above soil level at 3 years.

*Color*.—Near RHS Greyed-Green 197C with scales 197A. Bark Grey-Brown N199A.

*Surface Texture*.—Shallowly furrowed. Moderately scaly bark.

FOLIAGE

Leaf:

*Arrangement*.—Alternate.

*Shape*.—Narrow ovate.

*Average Length*.—Approximately 5 to 7 cm excluding petiole.

*Average Width*.—Approximately 2.5 cm.

*Apex*.—Acute.

*Base*.—Taper.

*Margin*.—Entire. 3 shallow, rounded protrusions present on each side.

*Texture of top surface*.—Glabrous.

*Texture of lower surface*.—Glabrous trichomes not observed in Fall.

*Appearance of top surface*.—Very glossy.

*Appearance of lower surface*.—Matte.

*Color*.—Young foliage: Upper side: Near RHS Green 137D. Under side: Near RHS Yellow-Green 145B. Mature foliage: Upper side: Near RHS Green 139A. Under side: Near RHS Green 139D.

*Venation*.—Type: Pinnate. Color: Venation color upper side: Near RHS Yellow-Green 144D. Venation color under side: Near RHS Yellow-Green 145A.

*Petiole*.—Length: Average 7 mm. Diameter: Average 2 mm. Color: Upper side: Near RHS Greyed-Purple N186C. Under side: Near RHS Greyed-Orange 176A.

FLOWER

Not observed to date.

REPRODUCTIVE ORGANS

Not observed.

OTHER CHARACTERISTICS

Disease/Pest resistance: Neither resistance nor susceptibility to other normal diseases and pests of *Quercus* has been observed.

Drought Tolerance: No tolerance for drought observed.

Temperature tolerance: USDA Zones 8 through 10.

Fruits/Nuts: Not observed to date.

What is claimed is:

1. A new and distinct cultivar of *Quercus virginiana* tree named 'QVMTF2' as herein illustrated and described.

* * * * *